United States Patent [19]

Flockenhaus et al.

[11] 4,259,312
[45] Mar. 31, 1981

[54] PROCESS AND APPARATUS FOR CATALYTICALLY REACTING A REDUCING GAS AND WATER VAPOR

[75] Inventors: Claus Flockenhaus, Essen-Haarzopf; Erich Hackler, Kettwig, both of Fed. Rep. of Germany

[73] Assignees: Didier Engineering GmbH, Essen; Thyssengas GmbH, Duisburg-Hamborn, both of Fed. Rep. of Germany

[21] Appl. No.: 81,615

[22] Filed: Oct. 3, 1979

Related U.S. Application Data

[63] Continuation of Ser. No. 895,464, Apr. 11, 1978, abandoned.

[30] Foreign Application Priority Data

Apr, 18, 1977 [DE] Fed. Rep. of Germany ....... 2717101

[51] Int. Cl.³ .................. B01J 3/03; B01J 12/00
[52] U.S. Cl. .................. 423/659; 423/210; 423/360; 423/437; 423/655; 423/656; 422/191; 422/192; 422/193; 422/203; 422/208; 422/242; 260/449.6 M
[58] Field of Search .............. 423/359–363, 423/210, 437, 655, 656, 659, DIG. 11, DIG. 16; 422/191, 192, 193, 203, 208, 242; 260/449 M, 449.6 M

[56] References Cited

U.S. PATENT DOCUMENTS

| | | | |
|---|---|---|---|
| 1,845,050 | 2/1932 | Lantz et al. | 423/360 |
| 1,909,442 | 5/1933 | Williams | 260/449 M |
| 3,392,001 | 7/1968 | Lorenz et al. | 423/656 |
| 3,498,752 | 3/1970 | Kuo | 422/294 |
| 3,663,179 | 5/1972 | Mehta et al. | 422/148 |
| 3,751,232 | 8/1973 | Borre et al. | 422/191 |
| 3,807,963 | 4/1974 | Smith | 422/203 |
| 4,152,407 | 5/1979 | Fuchs | 260/449 M |

FOREIGN PATENT DOCUMENTS 215436 6/1961 Austria .
2427530 12/1975 Fed. Rep. of Germany .

*Primary Examiner*—Earl C. Thomas
*Attorney, Agent, or Firm*—Wenderoth, Lind & Ponack

[57] ABSTRACT

An outer enclosed pressure container is formed of a simple steel material. An inner enclosed container is positioned within the pressure container such that there is an intermediate space therebetween. Catalyst layers are provided within the inner container. A gas containing a reducing component and water vapor are introduced into the inner container and are therein reacted by means of the catalyst to perform a desired reducing reaction. At least part of the water vapor is alone introduced into the intermediate space to thereby pressurize the intermediate space to substantially the same pressure as occurs within the inner container. The water vapor in the intermediate space operates to protect the wall of the pressure container from the temperatures occurring due to the catalytic reaction within the inner container. The water vapor is removed from the intermediate space and is at least partially added to the gas containing a reducing component before the introduction thereof into the inner container.

20 Claims, 1 Drawing Figure

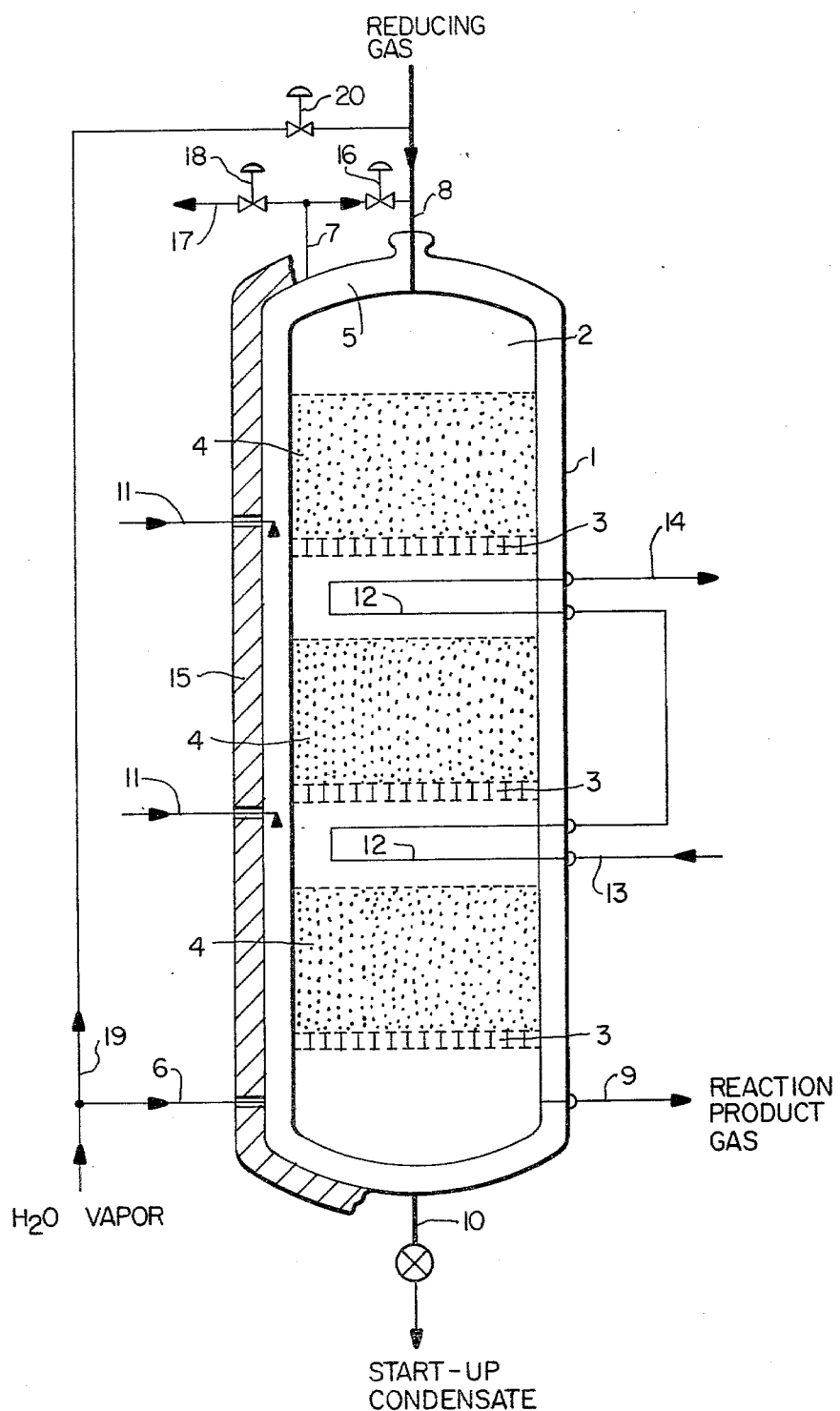

PROCESS AND APPARATUS FOR CATALYTICALLY REACTING A REDUCING GAS AND WATER VAPOR

This is a continuation, of application Ser. No. 895,464, filed Apr. 11, 1978 now abandoned.

BACKGROUND OF THE INVENTION

The present invention relates to a process and apparatus for catalytically reacting a gas containing a reducing component or components with water vapor in a pressure reactor of the type including an external pressure resistant container as well as an inner container containing a volume of catalyst.

Processes and apparatuses of the above type are known and are frequently employed for CO-methanization reactions and for CO-conversion reactions, as well as for reactions employing water vapor and other gases containing reducing components. Temperatures involved in such reactions are normally in the range of from approximately 623° K. to 723° K. (i.e. from 350° C. to 450° C.). The pressures involved in such reactions normally amount to approximately between 10 and 100 bar. Under such reaction conditions, i.e. quite high temperatures and pressures, the reducing components of the gases involved, for example carbon monoxide and hydrogen, may readily attack and penetrate the wall of the pressure resistant container, if such container is made of simple steel material, thereby leading to brittleness of the material and substantial premature corrosion damage.

Previous attempts to avoid such corrosion damage have involved the use of special alloy steels, particularly of the so-called pressure and hydrogen resistant type steels. Such special alloys steels are capable of withstanding the above described stresses. However, such special alloy steels involve certain inherent disadvantages which have prevented them from achieving widespread use. Specifically, such special alloy steels are extremely difficult to work. Additionally, such special alloy steels are extremely expensive, and this is an important disadvantage when considering the substantial size of the reactors involved.

Accordingly, most prior art reactors of this type have not employed such special alloy steels, but rather have employed simple steels, thereby resulting in substantial installation and repair costs due to premature corrosion damage.

German DT-OS 24 27 530 discloses a methanization reactor wherein the wall of the pressure container is shielded against the high exothermic temperatures that occur during the methanization reaction by means of an inner container containing at least a portion of the volume of the catalyst. The inner container is arranged within the pressure container with an intermediate space therebetween. The gas mixture to be reacted, consisting predominantly of methane and additionally containing carbon monoxide, carbon dioxide, hydrogen and water vapor required for the methanization reaction, is led through an inlet into the intermediate space around the inner container, and thus comes directly into contact with the wall of the outer pressure container. The gas then flows radially inwardly through the catalyst. It will be apparent that this type of reactor is associated with the above discussed disadvantages, namely that the reducing components of the gas are allowed to react on the wall of the pressure container. Therefore, this prior art device is still subject to the above discussed high cost of manufacture or to the danger of premature corrosion damage.

Austrian Pat. No. 215436 discloses a reactor having in the interior thereof plural intermediate limited spaces. The gas is divided into a number of partial flows and supplied to these intermediate spaces. One such gas flow cools the wall of the pressure container from the inside thereof. However, such partial flow is of the reaction gas itself and therefore includes reducing components. Accordingly, the wall of the pressure container is still subjected to the action of such reducing components, and accordingly this prior art device is also subject to the above discussed disadvantages.

SUMMARY OF THE INVENTION

With the above discussion in mind, it is the primary object of the present invention to provide a process and apparatus for catalytically reacting a gas containing reducing components with water vapor, wherein the pressure container may be formed of simple steel, while avoiding premature corrosion damage to the pressure container, thereby ensuring a more economical manufacture and operation of the pressure reactor than has heretofore been possible.

This object is achieved in accordance with the present invention by providing an outer pressure container formed of simple steel material, and an inner container also formed of simple steel material and containing the catalyst volume. The inner container is inwardly spaced from the outer pressure container to provide an intermediate space therebetween. The inner container is enclosed and the interior thereof is isolated from the intermediate space. The water vapor and the gas containing the reducing component or components are introduced into the inner container in a specific manner. More particularly, the gas containing the reducing components is introduced only to the inner container and is never introduced into the intermediate space. However, at least a portion of the water vapor is initially introduced into the intermediate space and is maintained at a pressure substantially equal to the pressure within the interior of the inner container. Thus, the inner container, although formed of simple steel and subjected to the reducing components, is not subjected to a unilateral high pressure. Rather, the pressures on both sides of the inner container are substantially equal. Furthermore, the water vapor passing through the intermediate space operates to protect the wall of the pressure container from the high temperatures occurring during the catalytic reaction within the inner container. The water vapor passes from the intermediate space, and then at least a portion of such water vapor is added to the gas containing the reducing components before the introduction thereof into the inner container.

Accordingly, although the pressure container is unavoidably subjected to a high pressure, the pressure container is protected against extremely high temperatures, and further the pressure container is never subjected to the reducing components. Thus, it is not necessary to employ expensive special alloy steels for the pressure container. Further, although the inner container is unavoidably subjected to the reducing components, the pressures on opposite sides of the container are substantially equal. Therefore, the inner container is less subject to corrosion which would otherwise occur at unilateral high pressures, and it is also unnecessary to form the inner container of expensive special alloy steels.

The passage of the water vapor through the intermediate space protects the wall of the pressure container against high temperature peaks which may occur in the catalyst within the inner container. Such high temperature peaks are prevented from affecting the pressure container by the continuous removal of heat from the intermediate space by the passage therethrough of water vapor. This avoids irregular thermal absorption by the pressure container and consequent irregular thermal expansion and differential stressing of the wall of the pressure container.

Additionally, during start-up of the reactor of the invention, the wall of the pressure container can be warmed up with pure water vapor passing through the intermediate space, prior to the introduction of the mixture of water vapor and gas containing reducing components into the reaction chamber of the inner container. Thus, any condensates which are formed in the intermediate space during the start-up operation do not contain harmful gas components, for example carbon monoxide, which would lead to corrosion. Further, any such condensates can be readily removed from the intermediate space before the commencing of normal operation.

BRIEF DESCRIPTION OF THE DRAWING

Other objects, features and advantages of the present invention will be apparent from the following detailed description thereof with reference to the accompanying drawing, wherein:

The single FIGURE is a schematic view of one embodiment of a pressure reactor in accordance with the present invention.

DETAILED DESCRIPTION OF THE INVENTION

The following description will generally be made with reference to a CO-conversion reaction, wherein an input gas contains carbon monoxide as a reducing component to be reacted with water vapor on a catalyst into hydrogen and carbon dioxide. It is specifically to be understood however that the scope of the present invention is not intended to be limited to such specific conversion reaction. Rather, the scope of the present invention is intended to encompass CO-methanization reactions, as well as any other conventional and known catalytic reactions involving the use of water vapor and a gas containing a reducing component.

It is further to be understood that the present invention is not directed to the specific catalysts employed, the specific gases employed, or to the specific temperatures and pressures involved. Rather, the present invention is directed to the novel process and apparatus described hereinbelow and intended to be employed in any otherwise conventional catalytic reaction employing known catalysts, known gases containing reducing components, and at temperatures and pressures which are conventional and known for such reactions.

In the drawing there is shown a pressure resistant pressure container 1 having positioned therein a closed inner container 2 containing therein a catalyst volume. Inner container 2 is inwardly spaced from pressure container 1 to define therebetween an intermediate space 5. In the illustrated embodiment there are shown three vertically separated catalyst layers 4, each supported on a catalyst support 3. It is specifically to be understood however that the present invention is not intended to be limited by the specific manner of location and placement of the catalyst. More particularly, the present invention may employ a greater lesser number of catalyst layers. Further, as stated above, the present invention is not intended to be limited to any specific catalyst. Catalysts employed in catalytic reactions of this type may be any known such catalysts, generally containing contact materials of iron mixtures.

Intermediate space 5 is isolated from the interior of inner container 2. A water vapor feed or inlet 6 opens into the intermediate space 5, preferably near the bottom portion thereof. A water vapor outlet 7 extends from intermediate space 5, preferably at the upper head portion thereof. An inlet 8 for supplying water vapor and a gas containing a reducing component or components extends through pressure container 1 and intermediate space 5 and opens into the interior of inner container 2. Inlet 8 does not open into intermediate space 5. A reaction product gas outlet 9 extends from the interior of inner container 2 through intermediate space 5 and pressure container 1. Outlet 9 does not communicate with intermediate space 5. An outlet 10 extends from the bottom of intermediate space 5 to remove therefrom condensates which may be formed during the start-up of the reactor. It will be understood that during normal operation of the reactor, condensate outlet 10 is closed.

One or a plurality of cooling devices 11 may extend through pressure container 1 and open into intermediate space 5. Such cooling devices are connected to a source of cooling fluid, for example water (not shown) and may include injection nozzles for injecting a cooling fluid into intermediate space 5 to cool the water vapor passing therethrough. In the illustrated embodiment, two such cooling devices 11 are shown, one each located in the general vicinity of the lower portion of the two upper catalyst beds, i.e. areas likely to be subjected to high temperature peaks. It is to be understood however that fewer or more cooling devices 11 could be provided.

Additionally, to control the heat within the reaction chamber of the inner container 2, i.e. the heat of reaction, indirect heat exchanger cooling devices 12 may be provided between adjacent layers of catalyst 4. Such cooling devices 12 may be connected through cooling inlet and cooling outlet pipes 13 and 14, respectively, to a conventional cooling system (not shown).

In order to obtain the smallest possible temperature variation of the wall of the pressure container during normal operation, and to thereby avoid to the greatest extent possible the condensation of the water vapor in intermediate space 5, the exterior of pressure container 1 may be covered by a relatively thick layer of conventional insulating material 15.

Water vapor outlet 7 which extends from the head portion of intermediate space 5 is connected via a valve 16 to gas inlet 8, at a position thereof exterior of the pressure container. Thus, valve 16 may be employed to regulate the amount of water vapor fed from intermediate space 5 to be mixed with the gas flow, dependent upon the requirements of the particular reaction involved. To remove any excess quantity of water vapor not necessary for the particular reaction involved, a return pipe 17 is connected to outlet 7 at a position upstream of valve 16. Return pipe 17 may lead back to inlet 6 or to a conventional steam generator. Return pipe 17 includes a valve 18 which may be employed to shut off entirely or to regulate the amount of flow through return pipe 17.

In the event that the quantity of steam passing through intermediate space 5 and joining gas inlet 8 via outlet 7 is insufficient for the requirements of the particular reaction involved, additional water vapor may be supplied to the gas inlet 8 via a water vapor bypass pipe 19. Bypass pipe 19 branches from inlet 6 and extends outwardly of pressure container 1 to join gas inlet 8 in the area of the head of the reactor. Bypass pipe 19 may be provided with a valve 20 to regulate the amount of additional water vapor required for the particular reaction involved.

The water vapor is preferably supplied superheated from an external steam generator through inlet 6 at a pressure of from approximately 16 to 101 bar and at a temperature of approximately from 500° to 700° K., during normal operation of the reactor. The pressure of the gas flow in gas inlet 8 is approximately the same as that of the water vapor within intermediate space 5, but preferably may be slightly lower, for example one bar lower, i.e. from between approximately 15 and 100 bar. However, the temperature of the gas flow through gas inlet 8 into inner container 2 is advantageously approximately 30° K. higher than the temperature of the water vapor, in order to attain the required ignition temperature when flowing through the catalyst. The exothermal heat generated by the mixture of gas and steam on the catalyst layers is controlled and throttled by means of cooling devices 12, so that a maximum temperature, for example 750° K. is not exceeded in the catalyst beds.

Although it is believed that the process of the present invention will be readily apparent from the above description, such process will become even further apparent from the following example.

EXAMPLE

During the start-up of the reactor, pure water vapor at a temperature of 623° K. and a low pressure of two bar is first fed through inlet 6 into intermediate space 5, for the purpose of warming up the wall of the pressure container 1. Steam condensate formed during such warm-up operation is removed through condensate outlet 10. Only after the pressure container 1 is satisfactorily warmed up, is the water vapor from outlet 7 passed into gas inlet 8 and is the gas containing reducing components supplied through gas inlet 8 into the interior of inner container 2. The gas fed through inlet 8 has a composition of approximately 29% by volume CO, 40% by volume $H_2$, 4% by volume $CO_2$, and 27% by volume $CH_4$. Such gas is supplied at a temperature of 653° K., and its pressure is intially temporarily just as low as that of the water vapor, i.e. approximately two bar. The gas, together with the admixed water vapor from outlet 7, directly enters inner container 2 and is therein serially reacted in the three catalyst layers 4. The pressure of the water vapor within intermediate space 5 and the mixture of water vapor and gas within the interior of inner container 2 are then slowly raised to the desired higher normal operational pressure level, for example to at least fifteen bar.

The heat generated during the catalytic reaction is removed and controlled by cooling devices 12 such that the temperature on the first or upper catalyst layer is maintained at approximately 723° K., at the second or central catalyst layer at approximately 703° K., and the third or lower catalyst layer at approximately 693° K. The water vapor flowing through the intermediate space 5 also operates to protect the wall of pressure container 1 from the high temperature generated within inner container 2. Additionally, injection of a cooling fluid such as water through cooling devices 11 into intermediate space 5 may additionally cool the water vapor, for example when substantial temperature peaks are generated in the catalyst beds which would otherwise superheat the steam to an undesirable extent.

The gaseous reaction products are removed from the reactor at an outlet temperature of 693° K. through outlet 9.

It is to be understood, as discussed above, that the present invention is suitable not only for CO-conversion reactions, but also for CO-methanization reactions, as well as for other reactions involving water vapor and a gas containing reducing components. The specific amount of water vapor required for each particular reaction, as well as the specific amounts of water vapor passed through intermediate space 5 in a given reactor may be readily regulated by suitable adjustment of valves 16, 18 and 20. To the gas flow in gas inlet 8, it is possible to admix as required the entire amount of water vapor flowing through intermediate space 5, or a portion thereof, with valve 20 closed, or when valve 20 is opened, it is possible to additionally admix an additional amount of water vapor required for the particular reaction involved.

Since the inner wall of the pressure container is subjected throughout the entire operation only to water vapor at a determinable pressure and at a constantly equalized temperature, the wall of the pressure container may be maintained free of chemical or physical corrosions which are inherent in prior art devices. Further, since the pressures on opposite sides of inner container 2 are equalized, it is also possible to reduce the danger of corrosion of the inner container. Accordingly, both the inner container and the pressure container may be formed of relatively inexpensive materials, and additionally the expense of maintaining the reactor will be substantially reduced.

It will be apparent that various modifications may be made to the specifically described and illustrated structural arrangements and process steps without departing from the scope of the present invention.

What we claim is:

1. A process for catalytically reacting water vapor with a gas containing at least one reducing component in a pressure reactor, to thereby produce a desired gaseous reaction product, said process comprising:

providing a pressure reactor including an outer pressure container and an inner container positioned within said pressure container, said inner container being inwardly spaced from said pressure container to define therebetween an intermediate space entirely surrounding said inner container, the interior of said inner container being isolated from said intermediate space;

providing within said inner container a catalyst required for the reaction;

introducing directly into said inner container, without introduction into said intermediate space and without contacting the inner surface of said outer pressure container, a mixture of the water vapor required for the reaction and the gas containing reducing components required for the reaction, whereby said water vapor and gas react in the presence of said catalyst to form a desired reaction product;

simultaneously introducing pure water vapor only into said intermediate space and passing said pure water vapor through said intermediate space; and removing said reaction product from said inner container.

2. A process as claimed in claim 1, wherein said pure water vapor which is passed through said intermediate space is at least in part added to said gas before introduction of said gas into said inner container to form said mixture.

3. A process as claimed in claim 2, further comprising adding to said gas, prior to introduction thereof into said inner container, a second portion of water vapor which is not previously passed through said intermediate space.

4. A process as claimed in claim 1, further comprising maintaining the pressure of said water vapor in said intermediate space substantially equal to the pressure within said inner container.

5. A process as claimed in claim 4, wherein said water vapor pressure in said intermediate space is approximately 16 to 101 bar.

6. A process as claimed in claim 5, wherein said gas pressure in said inner container is approximately 15 to 100 bar.

7. A process as claimed in claim 1, further comprising cooling said pure water vapor passing through said intermediate space.

8. An apparatus catalytically reacting water vapor with a gas containing at least one reducing component, to thereby produce a desired gaseous reaction product, said apparatus comprising:

an enclosed pressure resistant outer pressure container;

an enclosed inner container positioned within said pressure container and spaced inwardly therefrom to define therewith an intermediate space entirely surrounding said inner container, the interior of said inner container being completely isolated from said intermediate space;

a catalyst volume required from the reaction positioned entirely within the interior of said inner container;

a first supply means of a gas containing reducing components required for the reaction;

a second supply means of pure water vapor required for the reaction, said first supply mean being separate from said second supply means;

water vapor inlet means for introducing pure water vapor only from said second supply means through said outer pressure container into said intermediate space and passing said pure water vapor only through said intermediate space, while maintaining said pure water vapor at a predetermined high pressure and a predetermined high temperature, and for thereby providing means for protecting said outer pressure container from contact by said reducing component and from extremely high temperatures from said reaction;

water vapor outlet means for withdrawing said pure water vapor from said intermediate space outwardly of said outer pressure container;

gas inlet means for introducing gas from said first supply means through said outer pressure container and said intermediate space, without introduction into said intermediate space and without contacting the inner surface of said outer pressure container, directly into said inner container;

means for adding at least a portion of said pure water vapor withdrawn from said intermediate space to said gas in said gas inlet means at a position outwardly of said outer pressure container, and for thereby forming a water vapor-gas mixture within said gas inlet means, whereby said mixture is introduced at a pressure substantially equal to said predetermined high pressure into said inner container whereat said water vapor and gas react in the presence of said catalyst volume to form a desired reaction product;

means for maintaining the temperature within said inner container at a level on the same order as but slightly higher than said predetermined high temperature; and reaction product outlet means, extending from said inner container through said intermediate space and said outer pressure container, for removing said reaction product from said inner container without allowing introduction of said reaction product into said intermediate space.

9. An apparatus as claimed in claim 8, wherein said inner container is substantially equally spaced from said pressure container.

10. An apparatus as claimed in claim 8, further comprising first cooling means extending into said intermediate space for cooling said pure water vapor portion passing therethrough and for preventing superheating of said pure water vapor portion due to substantial temperature peaks generated in said catalyst volume.

11. An apparatus as claimed in claim 10, wherein said first cooling means comprises at least one injection nozzle positioned within said intermediate space for spraying thereinto a cooling fluid.

12. An apparatus as claimed in claim 11, wherein said catalyst volume is arranged in plural layers in said inner container.

13. An apparatus as claimed in claim 12, wherein said injection nozzles are located at positions adjacent all of said layers except the lowermost said layer.

14. An apparatus as claimed in claim 12, wherein said temperature maintaining means comprises second cooling means, extending into said inner container between adjacent said layers, for cooling the interior of said inner container.

15. An apparatus as claimed in claim 14, wherein said second cooling means comprise at least one indirect heat exchanger.

16. An apparatus as claimed in claim 8, wherein said temperature maintaining means comprises cooling means extending into said inner container for cooling the interior thereof.

17. An apparatus as claimed in claim 8, further comprising a layer of thermal insulation material surrounding the exterior of said pressure container.

18. An apparatus as claimed in claim 8, further comprising a water vapor return pipe connected to said water vapor outlet means, a first regulating valve in said water vapor outlet means at a position therein downstream of the connection thereto of said water vapor return pipe, and a second regulating valve in said water vapor return pipe.

19. An apparatus as claimed in claim 18, further comprising a water vapor bypass line extending from said water vapor inlet means to said gas inlet means, exterior of said pressure container, and a third regulating valve in said water vapor bypass line.

20. An appartus as claimed in claim 8, further comprising means, located exteriorly of said pressure container, for supplying a further portion of water vapor to said gas inlet means.

* * * * *